United States Patent
Robinson et al.

(10) Patent No.: US 11,209,428 B1
(45) Date of Patent: Dec. 28, 2021

(54) DIAGNOSTIC TEST FOR VACCINE VALIDATION AND AUTHENTICATION AND METHODS OF USE THEREOF

(71) Applicant: QUANTUM MATERIALS CORPORATION, San Marcos, TX (US)

(72) Inventors: Andrew Robinson, San Marcos, TX (US); Krishna Kowlgi, San Marcos, TX (US); Stephen Squires, San Marcos, TX (US); Brent Wade Ferguson, San Marcos, TX (US); Nathanael J. Barree, San Marcos, TX (US)

(73) Assignee: Quantum Materials Corporation, San Marcos, TX (US)

( * ) Notice: Subject to any disclaimer, the term of this patent is extended or adjusted under 35 U.S.C. 154(b) by 0 days.

(21) Appl. No.: 17/321,194

(22) Filed: May 14, 2021

Related U.S. Application Data

(60) Provisional application No. 63/183,100, filed on May 3, 2021.

(51) Int. Cl.
*C12Q 1/6804* (2018.01)
*G01N 33/543* (2006.01)
*G01N 33/569* (2006.01)

(52) U.S. Cl.
CPC ..... *G01N 33/54388* (2021.08); *C12Q 1/6804* (2013.01); *G01N 33/56983* (2013.01); *G01N 2333/165* (2013.01)

(58) Field of Classification Search
CPC ....... G01N 33/54388; G01N 33/56983; G01N 2333/165; C12Q 1/6804
See application file for complete search history.

(56) References Cited

U.S. PATENT DOCUMENTS

2008/0199851 A1* 8/2008 Egan ............... B01L 3/5029
435/5

\* cited by examiner

*Primary Examiner* — Jennifer Wecker
*Assistant Examiner* — Michael Paul Shimek
(74) *Attorney, Agent, or Firm* — Cooley LLP

(57) ABSTRACT

The present invention encompasses a diagnostic test and method to authenticate the veracity of a vaccine. The diagnostic test and method are especially useful in a specific and sensitive immunochromatographic assay, performable within about 15 minutes for the authentication, validation, and veracity of a vaccine, such as a COVID-19 vaccine, in a vial prior to administration to a human.

16 Claims, 5 Drawing Sheets

DIAGNOSTIC TEST FOR VACCINE VALIDATION AND AUTHENTICATION AND METHODS OF USE THEREOF

I. FIELD OF THE INVENTION

The present invention encompasses a diagnostic test and method to authenticate the veracity of a vaccine. The diagnostic test and method are especially useful in a specific and sensitive immunochromatographic ("ICT") assay, performable within about 15 minutes, for the authentication, validation, and veracity of a vaccine in a vial prior to administration to a human, such as a COVID-19 vaccine.

II. BACKGROUND OF THE INVENTION

Reports of counterfeit versions of vaccines for COVID-19 have been reported in Mexico and Poland. Fueled by the ease and convenience of e-commerce and anonymity afforded by the Internet, there will be an increase in the prevalence of fraud, counterfeit and other illicit activity as it relates to vaccines and treatments for COVID-19. A rapid diagnostic test (RDT) is a medical diagnostic test that is less time consuming and less labor intensive than enzyme-linked immunosorbent assay (ELISA) or polymerase chain reaction (PCR) tests that must be sent to laboratories for analysis. RDTs are suitable for preliminary and/or emergency medical screening, for example, for use in medical facilities with limited resources, and offer a useful alternative to microscopy in situations where reliable microscopic diagnosis facility is not available or is not immediately available. RDTs also allow point-of-care (POC) testing in primary care. RDTs do not require clinical diagnostic methods, such as ELISA or PCR. RDTs can be performed independent of laboratory equipment by minimally trained personnel, and deliver rapid results. RDTs provide results within two hours, and typically provide results in approximately 15-30 minutes.

An RDT employs a dipstick or cassette format for testing a specimen, such as a vaccine sample. For testing, the specimen is collected from a purported authorized vaccine, a sample pad on a test strip (or card) of the RDT dipstick or cassette along with certain reagents. Depending on the type of test that is being conducted, after a determined period of time, the presence or absence of specific bands in a test strip window indicates whether a sample is authentic or counterfeit. Generally, a drop of the specimen is added to the RDT device through a sample well, and then a buffer is usually added through a buffer well. The buffer carries the biological specimen along the length of the RDT device.

There is a need for RDTs to authenticate the vaccines that are being administered on a global scale to billions of individuals to ensure the personal health of the individual as well as community health.

III. SUMMARY OF THE INVENTION

In one embodiment, the invention encompasses a rapid diagnostic testing device for rapid diagnostic testing of a vaccine sample to determine the authenticity of the vaccine. The device comprises a channeled construct configured to receive a sample from the vaccine sample lot; at least one lateral flow unit is operatively coupled to the channeled construct and a cassette housing comprising a sample well, a first surface and a second surface, wherein the lateral flow unit is at least partially disposed in the cassette housing. The lateral flow unit comprises a sample receiving zone operatively coupled to the channeled construct for receiving the vaccine sample from the channeled construct, wherein the sample comprises at least one vaccine (e.g., an mRNA, a recombinant DNA vaccine, or a purified protein that is encoded by the genetic sequence of the SARS-CoV-2 spike (S) protein) and wherein the sample receiving zone comprises a first side and a second side; a conjugate zone adjacent to the first side of the sample receiving zone, wherein the conjugate zone comprises a conjugate particle for binding with the analyte; and a detection zone adjacent to the second side of the sample receiving zone, wherein the detection zone comprises at least one binding agent for detecting the analyte by capturing the analyte.

In another embodiment, the invention encompasses a lateral flow assay device for and a method for authenticating a vaccine comprising detecting the presence or absence of at least one target nucleic acid in a fluid vaccine sample, said device having a first and second end and comprising: a sample receiving zone at or near said first end for receiving an aliquot of said vaccine sample and comprising a porous material having first and second oligonucleotide probes coupled to first and second binding partners, respectively, wherein said probes specifically hybridize to said target nucleic acid to form a complex having said first and second binding partners, said sample receiving zone being in lateral flow contact with a labeling zone comprising a porous material having at least a first visible moiety reversibly bound thereto and coupled to a first ligand which specifically binds to said first binding partner to form a visible complex, said labeling zone including quantum dots and being in lateral flow contact with a capture zone comprising a microporous membrane which contains in a portion thereof a first capture moiety immobilized thereto which specifically binds said second binding partner, said capture zone being in lateral flow contact with an absorbent zone positioned at or near the second end of said device, wherein said visible complex is captured by said capture moiety in said portion of the capture zone.

FIG. 1 is an exemplary schematic of the lateral flow immunochromatographic assay in a housing. The sample pad is where the analyte (sample from a vaccine bottle) is introduced along with a running buffer (FIG. 2). This mixture soaks the sample pad and transfers into the conjugation pad which contains biomarkers (fluorophore such as quantum dots conjugated to antibodies). If the analyte is a genuine vaccine containing genuine vaccine, then these vaccine materials will bind to the biomarkers and flow together along the reaction pad to the test line and be arrested by capture antibodies there leading to the appearance of a fluorescent line. This fluorescent line confirms that the vaccine sample is authentic. Meanwhile the matrix line validates another other component of the vaccine such as the adjuvant. Any uncaptured analyte or unbound biomarkers will be soaked to the absorbent pad.

FIG. 2 illustrates the components of an exemplary vaccine validator: 1. Lateral flow test cassette as described in FIG. 1. 2. Running buffer to prepare the analyte and make it flow on the test cassette. 3. Fluid vial with cap is where the analyte and running buffer are premixed before introduction into the lateral flow test cassette. 4. Violet flashlight to illuminate the test lines on the test strip (FIG. 1).

In accordance with exemplary aspects described in this specification, a diagnostic system includes a multiplexed lateral flow test cassette, a data reader, and optionally a smart phone or tablet. In certain embodiments, the multiplexed lateral flow test cassette comprises a lateral flow immunochromatographic assay and can include a housing, a test strip, and a QR code or other identifier, which may be readable by a sensor, such as an optical sensor on a smartphone or other device. In certain embodiments, the lateral flow immunochromatographic assay is a biochemical test that measures (qualitatively/semi-quantitatively) the presence and authenticity of a vaccine (such as a SARS-CoV-2 vaccine) with the help of sensory molecules (based on quantum dots/nanoparticles) on a platform (e.g., a membrane that controls the transport of the molecules) that displays a visual pattern when a successful test run occurs. Optionally, this visual pattern on the test strip in combination with a machine-readable code (e.g., a QR code or similar code) that is coated on the assay housing (and packaging) and is used to determine the result of the diagnosis. The diagnostic system can also include accessories, including a fluid vial, a test swab, and a PBS buffer.

In certain embodiments, the data reader includes a data and power connector and a camera sensor inside a body of the data reader. In certain embodiments, a light source (e.g., LEDs) is integrated with the camera sensor for illuminating the test cassette to enable the camera sensor to detect test results from the test strip of the lateral flow test cassette. The data reader holds the test cassette in place and uses a combination of the camera sensor and light source to activate and read the spectral signature of the visual pattern on the test strip (e.g., quantum dots) and to read the machine-readable code. To hold the test cassette in place, the data reader can include a slot into which the test cassette or test strip can be inserted and which appropriately positions the test cassette so that the camera sensor can detect the visual pattern on the test strip. The use of a power connector avoids the need for battery power, which can help reduce the cost of the data reader and, along with using biodegradable housing materials, make the data reader more environmentally friendly and disposable.

In certain embodiments, the data reader communicates with a smartphone or other computing device. For example, the data reader can be connected to the charging port of a smartphone or tablet. The smartphone or tablet can both power the data reader and provide a communications channel. An app on the smartphone or tablet provides instructions for a human tester to perform the test, receives data from the reader and processes the data. The app can also instruct the tester to redo the test if the test is invalid or inconclusive, issue the test result, and provide further instructions, if needed.

In certain embodiments, the vaccine authenticity kit may include a lateral flow test cassette, a swab, a fluid vial with cap, and a PBS (phosphate-buffered saline) buffer or extraction fluid for use in performing a test. The lateral flow test cassette includes a housing that fits the reader in one orientation and prevents usage of fake cassettes. The test strip inside of the lateral flow test cassette housing includes a sample pad (e.g., where a vaccine sample is placed), a conjugation pad (e.g., containing antibody-nanoparticle conjugates), a reaction pad (e.g., where test result lines and a control line appear, and an absorbent pad. When a vaccine sample is placed on the sample pad, the sample flows along the test strep passing through the conjugate pad into the nitrocellulose membrane, which includes test and control lines, and then to the absorbent pad, which helps with the flow of the sample across the test strip. The test lines appear when a specific vaccine is present in the sample. The sample pad can use standard glass fiber/cellulose material, the conjugate pad uses unique antibodies and biolabels as described in this specification, the reaction pad can use a standard membrane (e.g., produced by Sartorius/GE), and the absorbent pad can use standard glass fiber/cellulose. The lateral flow test cassette optionally also includes a QR code that can be used to serialize data for uniquely identifying the test kit, identifying the type of test, and/or decoding what specific spectral patterns represent if they appear on the reaction pad.

In certain embodiments, the data reader may be included as part of a single use test kit or as part of a package of multiple test kits. The data reader can be designed to be reused for multiple tests (unlike many existing test readers). The data reader includes a housing, internal camera, internal LEDs for illuminating the test strip when inserted into the data reader, and an interface cable and adapter for connecting to one or more types of smartphones or tablets.

In alternative implementations, a camera sensor on a smartphone or tablet can be used to detect the visual pattern on the test strip instead of using a separate data reader. Although potentially more complex because of variations in ambient lighting, angular positioning of the camera sensor relative to the test cassette, differences among camera sensors from various suppliers (e.g., differing spectral sensitivities, focal lengths, and color gamuts), and the like, the app can be programmed to process images detected by the camera sensor to normalize the spectral data received from the camera sensor for further processing of the spectral signature to obtain test results.

Implementations of the test strip of the diagnostic system can use quantum dots as bio-labels. In certain embodiments, by replacing the signal marker on the LFIAs from ubiquitously used colloidal gold with quantum dots, the sensitivity and specificity can be improved.

In certain embodiments, the quantum dots also help achieve high performance. While colloidal gold nanoparticles are relatively large (>25 nm in size) biolabels used in sensing, the diagnostic system described in this specification can use novel biolabels (e.g., quantum dots and metal nanoclusters) that are much smaller (<5 nm). These biolabels can therefore, on an equivalent volume basis, offer more surface area. When conjugated with sensory proteins (e.g., antibodies), these biolabels can offer 3 orders of magnitude more binding sites for the analyte proteins (antibodies), which leads to highly improved sensitivity. These novel biolabels also offer various advantages such as higher luminosity, a gamut of distinct colors for multiplexing tests, consistency in manufacturing, longer shelf life, and orders of magnitude cost savings over colloidal gold.

Fluorescent nanoparticle labelled LFIAs have higher sensitivity and allow for in situ monitoring compared with LFIAs that use colloidal gold (CG) for the bio-labels. LFIAs labeled with fluorescent nanoparticles (e.g., quantum dots or fluorescent nanoclusters) have high quantum yields >35%, which enhances readability. In particular, test lines are easier to read and maintain readability much longer than CG-based LFIAs, which have low luminosity resulting from quantum yields <1%, making test lines difficult to read and which causes them to grow more faint with time. Fluorescent nanoparticle-labelled LFIAs also have a wide color gamut (potentially approaching or exceeding a million colors), which makes multiple analyte testing (multiplexing) possible. The limited color gamut (i.e., red and purple) of CG-based LFIAs makes multiplexing difficult. Furthermore, fluorescent nanoparticle-labelled LFIAs have a higher inherent stability over gold, which enhances durability, manufacturing consistency and shelf life of the LFIAs, and a lower cost of manufacture as compared to CG LFIAs.

The fluorescent nanoparticle labelled LFIAs can use quantum dots (such as CdSe/CdS tetrapod quantum dots)/ metal (such as Ag) nanocluster technology that requires special manufacturing equipment (e.g., a microflow reactor) that prevents production of counterfeit test strips (i.e., because the quantum dot composition cannot be duplicated). The data reader can include a spectrometer for accurately detecting spectral signatures of the quantum dots and can be tuned to be sensitive only to quantum dots that produce specific spectral responses expected from the authorized quantum dots or can provide the spectral information for software analysis (e.g., by the app). The software in the app can be tuned to analyze the spectral information received from the data reader to be able to distinguish counterfeit test strips from authentic test strips. Thus, the test strips avoid problems with existing diagnostic tests, in which similar looking alternatives can be used to produce counterfeit test strips, as most of the components are readily available worldwide with little or no differentiation.

In certain embodiments, the vaccine sample of appropriate concentration is introduced along with a phosphate buffer solution (PBS) as a drop on the sample pad. The assembly of antibody+antigen+QD (quantum dots) are collectively transported through the reaction pad and to the corresponding test line 1. T1, 2. T2, 3. C, where they bind with immobilized primary antibodies and form a single bright colored band (e.g., to indicate a positive test result corresponding to the test line). In certain embodiments, the control line could be designed to indicate presence of lysozymes. Unbound antibody+biolabels flow to the absorbent pad.

In certain embodiments, the LFIAs typically have a control line whose function is to indicate that lateral flow has occurred. The test strip of the modular diagnostic system described in this specification uses a control line that confirms lateral flow but that also functions as an indicator for the amount of vaccine sample introduced into the test cassette. This is useful for testers to perform the test without the help of a medical professional and to eliminate misuse. Current generation test strips have a control line which lights up only when the free gold nanoparticles flow to and immobilize on it. In a lit condition, it confirms for presence of buffer, functioning of the nanoparticles and the flow of both. But it does not account for the absence of sample (analyte) or insufficient analyte.

The modular diagnostic system can also enable use by testers who are not skilled in reading the lateral flow test, such as use in the home and by untrained users. Current LFIAs can require the tester to be skilled in reading the lateral flow test or to learn the skill by reading a manual. The modular diagnostic system includes a user-friendly app on a smartphone to guide the tester and a data reader device with electronics optimized to perform and analyze the lateral flow test preventing improper use of the test and loss of test result integrity. For example, a slot in the data reader can be shaped to prevent improper insertion of the test cassette by allowing insertion only in the proper orientation and the app can provide step-by-step instructions with graphics to guide the tester throughout the testing process.

The diagnostic system is economical and scalable to $10^9$/year scale or more. The smartphone/tablets can be provided by the tester and are ubiquitous. The app for the smartphone/tablets can be downloaded from the popular app stores. The data reader is made using inexpensive/recyclable/biodegradable plastic and its components (camera module, LED light source, and spectrometer) are cheap to build/source. Finally, the lateral flow test cassettes are already being built economically in the billion unit/year scale.

The diagnostic system can also be made to be disposable and biodegradable. Besides the smartphone/tablet and app module of the diagnostic system, the other two modules are disposable and biodegradable. Biodegradable plastic can be used for the test cassette and data reader housing. The test strip in the test cassette uses biodegradable components except for the biolabels which, if made using non-hazardous quantum dots or metal clusters, can be disposable. The data reader components (camera and LED light source) can also be made to be certified as disposable in household waste.

In certain embodiments, the invention encompasses a rapid diagnostic testing device for rapid authentication of a COVID-19 vaccine, comprising:

a sample receiving zone, wherein the sample receiving zone comprises a first side and a second side;

a conjugate zone disposed adjacent to the first side of the sample receiving zone, wherein the conjugate zone comprises a conjugate particle comprising at least one of quantum dot or metal nanocluster biolabels for binding with the analyte; and a detection zone disposed adjacent to the second side of the sample receiving zone, lateral flow assay device is used for detecting the presence or absence of at least one single-stranded target nucleic acid in a fluid sample, said device having a first and second end and comprising:

a sample receiving zone at or near said first end for receiving an aliquot of said sample and comprising a porous material having first and second oligonucleotide probes coupled to first and second binding partners, respectively, wherein said probes specifically hybridize to said target nucleic acid to form a complex having said first and second binding partners, said sample receiving zone being in lateral flow contact with a labeling zone comprising a porous material having at least a first visible moiety reversibly bound thereto and coupled to a first ligand which specifically binds to said first binding partner to form a visible complex, said labeling zone being in lateral flow contact with a capture zone comprising a microporous membrane which contains in a portion thereof a first capture moiety immobilized thereto which specifically binds said second binding partner, said capture zone being in lateral flow contact with an absorbent zone positioned at or near the second end of said device, wherein said visible complex is captured by said capture moiety in said portion of the capture zone, wherein the labeling zone includes one or more quantum dots.

In other embodiments the invention encompasses methods for authenticating the veracity of a COVID-19 vaccine, which vaccine includes a nucleic acid comprising contacting a sample of vaccine with a lateral flow assay device, which lateral flow assay device is used for detecting the presence or absence of at least one single-stranded target nucleic acid in a fluid sample, said device having a first and second end and comprising:

a sample receiving zone at or near said first end for receiving an aliquot of said sample and comprising a porous material having first and second oligonucleotide probes coupled to first and second binding partners, respectively, wherein said probes specifically hybridize to said target nucleic acid to form a complex having said first and second binding partners, said sample receiving zone being in lateral flow contact with a labeling zone comprising a porous material having at least a first visible moiety reversibly bound thereto and coupled to a first ligand which specifically binds to said first binding partner to form a visible complex, said labeling zone being in lateral flow contact with a capture zone comprising a microporous membrane which contains in a portion thereof a first capture moiety immobilized thereto which specifically binds said second binding partner, said capture zone being in lateral flow contact with an absorbent zone positioned at or near the second end of said device, wherein said visible complex is captured by said capture moiety in said portion of the capture zone, wherein the labeling zone includes one or more quantum dots.

In certain embodiments, the sample receiving zone porous material retains said probes prior to contact with said fluid sample and releases said probes after contact with said fluid sample.

In certain embodiments, the sample receiving zone porous material is selected from the group consisting of glass, cotton, cellulose, polyester, rayon, nylon, polyethersulfone, and polyethylene.

In certain embodiments, the first and second binding partners are selected from the group consisting of antibodies or fragments thereof, proteins, haptens, antigens or fragments thereof, avidin, streptavidin, biotin, fluorescein, isothiocyanate, folic acid, folate binding protein, protein A, protein G, immunoglobulins, digoxigenin, anti-digoxigenin F(ab')2, complementary nucleic acid segments, protein A, protein G, immunoglobulins, lectin, carbohydrate, enzymes, viruses, maleimides, haloacetyl derivatives, isotriocyanates, succinimidyl esters, sulfonyl halides, steroids, halogens and 2,4-dinitrophenyl.

In certain embodiments, the labeling zone porous material is selected from the group consisting of glass, cotton, cellulose, polyester, polyethylene, rayon or nylon.

In certain embodiments, the first visible moiety comprises a ligand coupled to one or more microparticle.

In certain embodiments, the microparticle is selected from the group consisting of polymers or copolymers of olefinically unsaturated monomers, glass, acrylamide, methacrylate, nylon, acrylonitrile, polybutadiene, metals, metal oxides and their derivatives, dextran, cellulose, liposomes, red blood cells, pollens, quantum dots, and bacteria.

In certain embodiments, the capture zone membrane comprises a microporous material selected from the group consisting of nitrocellulose, polyethersulfone, polyvinylidine fluoride, nylon, charge-modified nylon, and polytetrafluoroethylene.

In certain embodiments, the first capture moiety is selected from the group consisting of antibodies or fragments thereof, proteins, haptens, antigens or fragments thereof, avidin, streptavidin, biotin, fluorescein isothiocyanate, folic acid, folate binding protein, protein A, protein G, immunoglobulins, digoxigenin, anti-digoxigenin F(ab')2, complementary nucleic acid segments, protein A, protein G, immunoglobulins, lectin, carbohydrate, enzymes, viruses, maleimides, haloacetyl derivatives, isotriocyanates, succinimidyl esters, sulfonyl halides, steroids, halogens and 2,4-dinitrophenyl.

In certain embodiments, the capture zone is prepared by applying a solution containing said capture moiety to said membrane under conditions wherein the capture moiety becomes immobilized on said membrane, followed by drying said membrane.

In certain embodiments, the solution is applied to said membrane in the form of a line.

In certain embodiments, the labeling zone further comprises a second visible moiety reversibly affixed to said matrix and coupled to a second ligand, and said capture zone further comprises in a portion thereof a second capture moiety immobilized thereon which specifically binds said second ligand.

In certain embodiments, the portion of said capture zone containing said first capture moiety is separate from said portion containing second capture moiety.

In certain embodiments, the absorbent zone comprises a material selected from the group consisting of nitrocellulose, cellulose esters, glass, polyethersulfone, and cotton.

In certain embodiments, the entire test strip except for a portion of said sample receiving zone is completely sheathed in a transparent film.

IV. BRIEF DESCRIPTION OF THE FIGURES

V. DETAILED DESCRIPTION OF THE INVENTION

Figure 1:
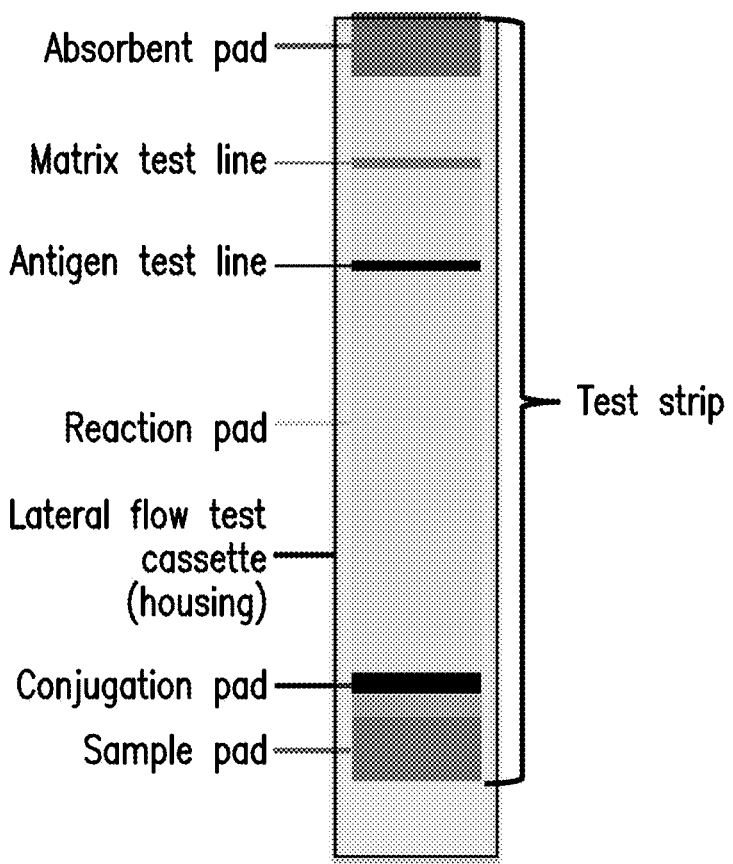
FIG. 1 is a schematic of an exemplary lateral flow immunochromatographic assay in a housing.
Figure 2:
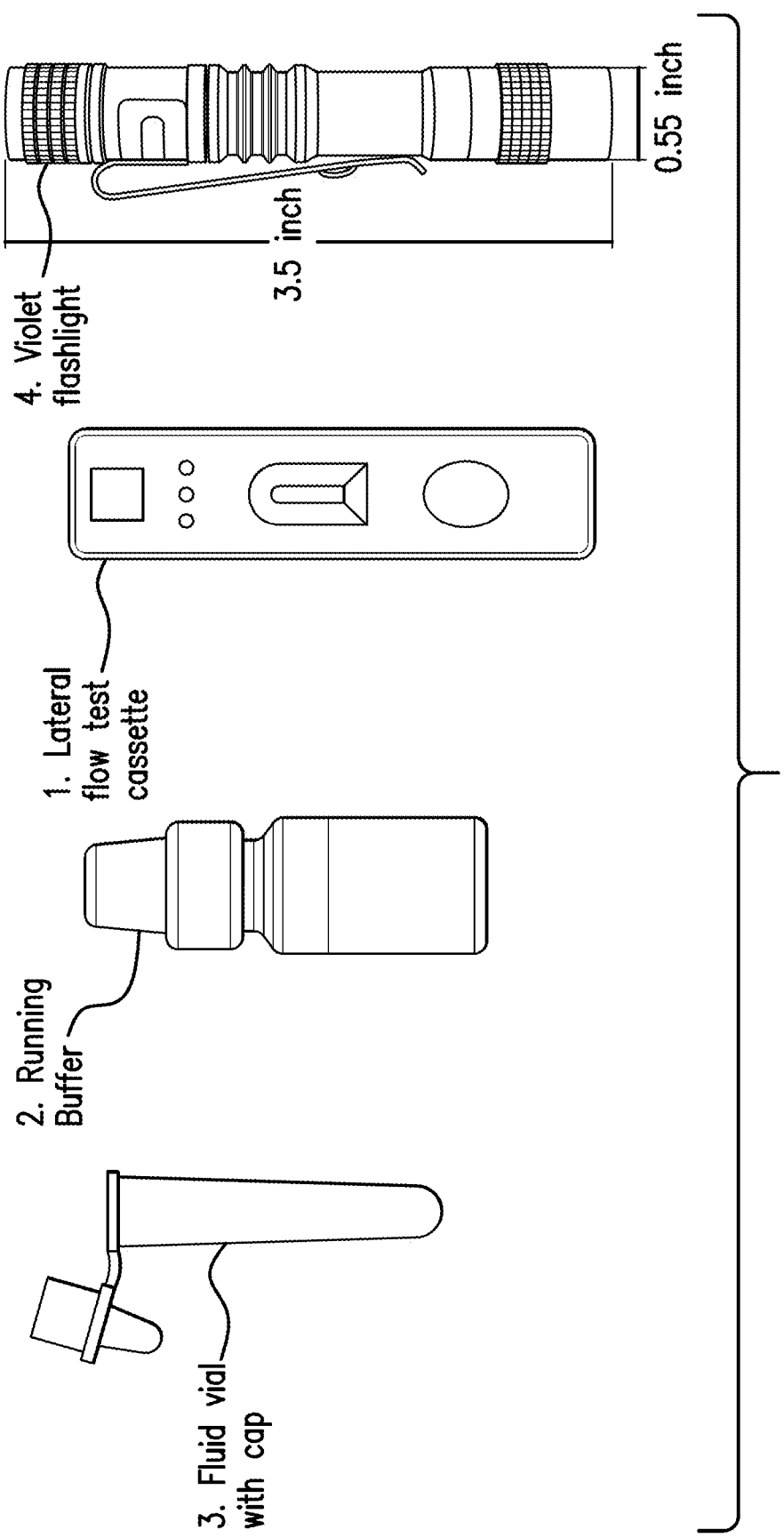
FIG. 2 illustrates the components of an exemplary vaccine validator.
Figure 3:
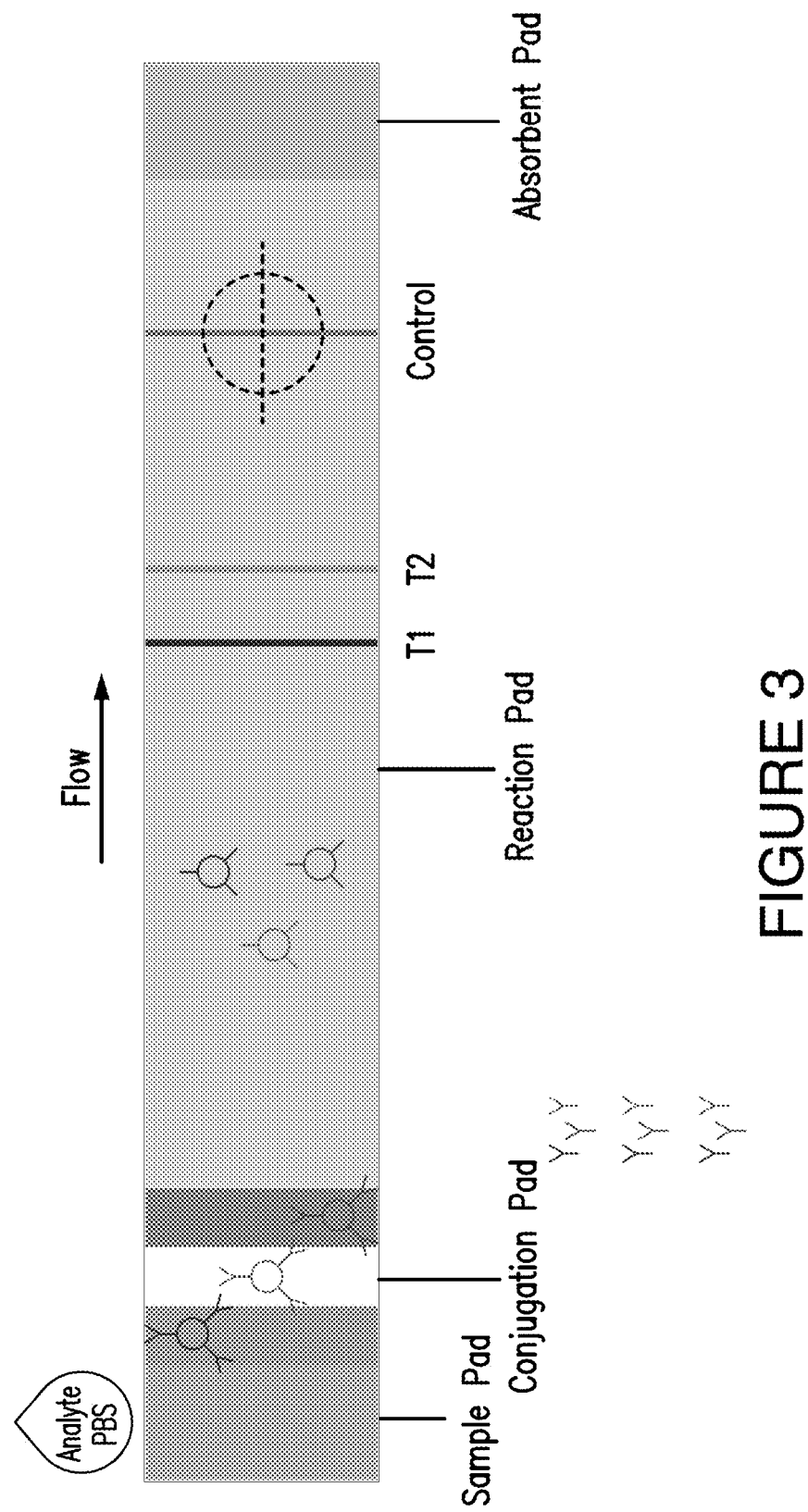
FIG. 3 is a representation of a test strip illustrating the principle of operation of one implementation of the diagnostic system.
Figure 4:
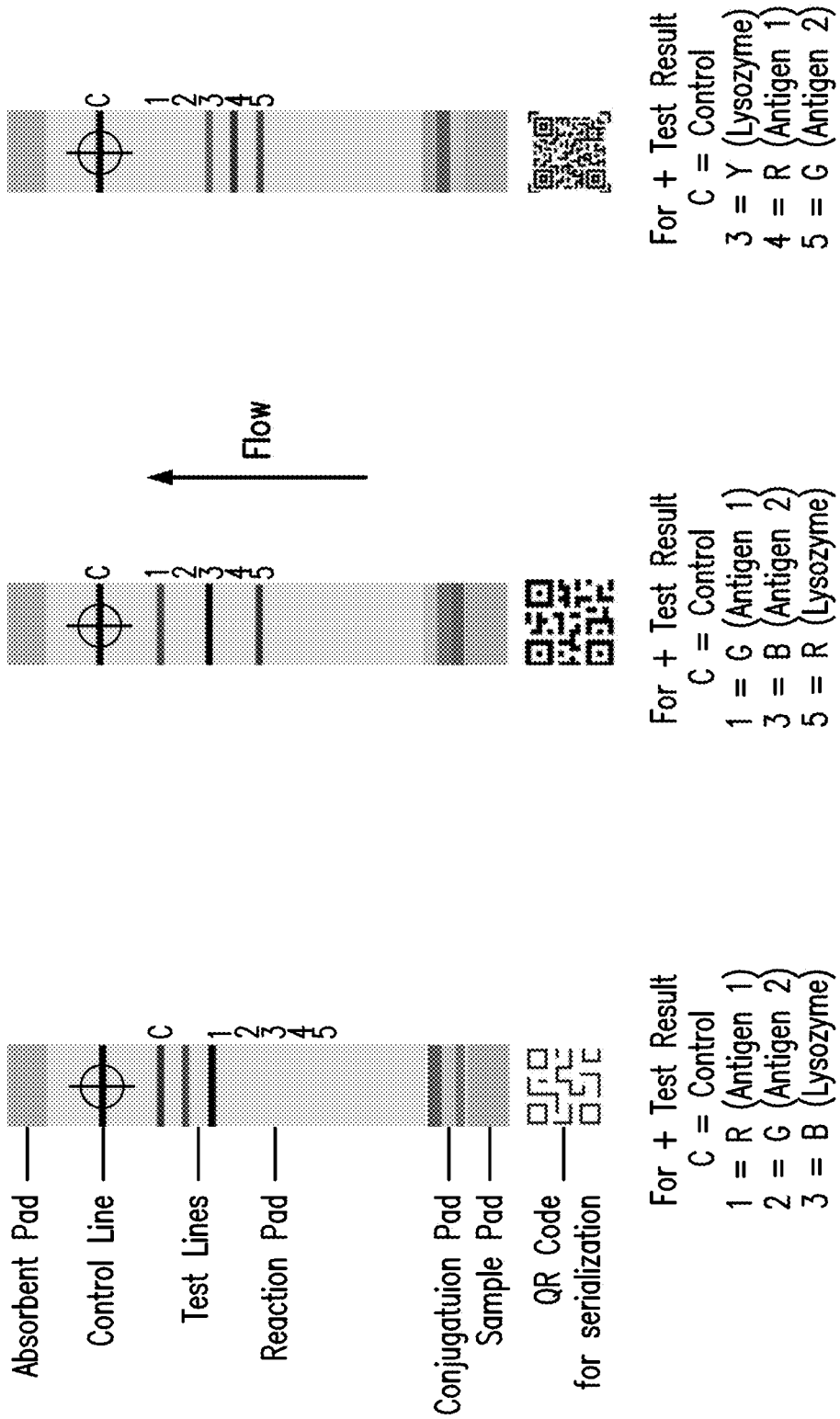
FIG. 4 is a depiction of different configurations of test strips implementing a testing capability.
Figure 5:
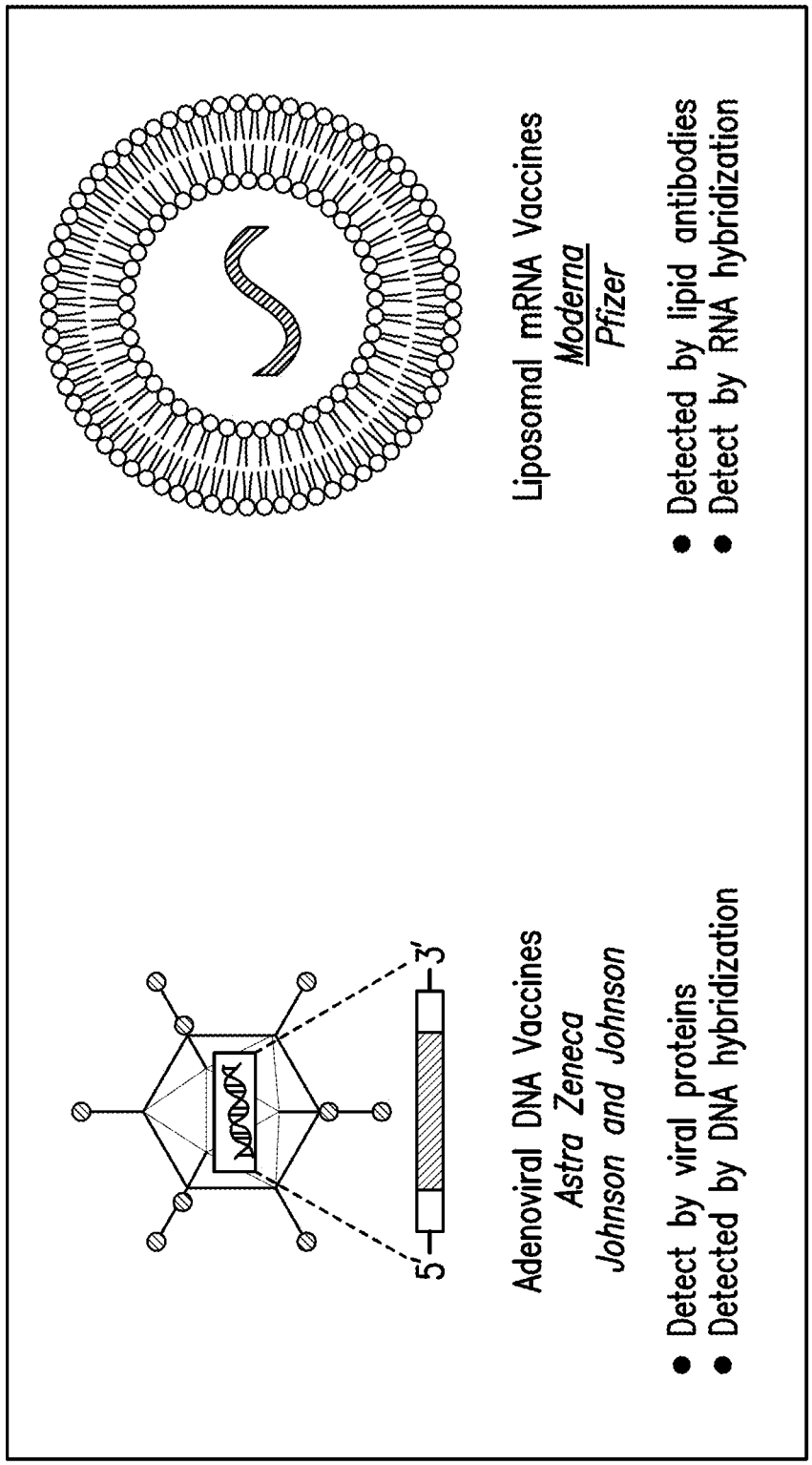
FIG. 5 is an illustration of authentication detection methods based on current AAV-DNA Vaccines and LNP-mRNA vaccines.

In certain embodiments, the invention encompasses a diagnostic testing device for rapid diagnostic testing to authenticate the veracity of a vaccine. In certain embodiments, the device comprises a channeled construct configured to receive at least a portion of a vaccine from a vaccine sample lot; at least one lateral flow unit operatively coupled to the channeled construct; and a cassette housing comprising a sample well, a first surface and a second surface, wherein the lateral flow unit is at least partially disposed in the cassette housing. The lateral flow unit comprises: a sample receiving zone operatively coupled to the channeled construct for receiving at least a portion of the vaccine sample vial, and wherein the sample receiving zone comprises a first side and a second side; a conjugate zone disposed adjacent to the first side of the sample receiving zone, wherein the conjugate zone comprises a conjugate particle for binding with the analyte to form an analyte-conjugate complex; and a detection zone disposed adjacent to the second side of the sample receiving zone, wherein the detection zone comprises at least one binding agent for detecting the analyte by capturing the analyte.

In another embodiment, a diagnostic testing device for rapid diagnostic testing of a vaccine sample is provided herein. The device comprises at least one lateral flow unit and a cassette housing comprising a sample well; wherein the lateral flow unit is at least partially disposed in the cassette housing. The lateral flow unit comprises: a sample receiving zone, wherein the sample receiving zone comprises a first side and a second side, a conjugate zone disposed adjacent to the first side of the sample receiving zone, wherein the conjugate zone comprises an antibody for binding with the antigen to form an antigen-antibody complex; and a detection zone disposed adjacent to the second side of the sample receiving zone, wherein the detection zone comprises a test region comprising a secondary antibody disposed on the test region for detecting the antigen by capturing the antigen-antibody complex.

Rapid diagnostic tests (RDTs) or rapid diagnostic testing devices (RDT devices) broadly include lateral flow assays (LFAs) and/or flow through assays (FTAs). RDTs or RDT device using LFAs are provided herein, wherein the LFAs are used for detection of analytes, such as different biomarkers present in a vaccine sample by immunochromatographic antigen-detection tests. In certain embodiments, the immunochromatographic antigen-detection tests of the invention rely on capture of analytes (antigens) by dye-labeled or quantum dot labeled antibodies to produce a visible band on a lateral flow assay unit, such as a nitrocellulose test strip. The lateral flow assay unit is encased in a housing, referred to as a cassette. For RDTs, in one aspect, the dye-labeled or quantum dot labeled antibody or conjugate particle-coupled antibody binds to an analyte (antigen) such as a vaccine biomarker. The resultant analyte-antibody complex is further captured by the binding agents (secondary antibody) on a test line of the lateral flow unit, forming a visible test line in a result window of the RDT device. In another aspect, the analytes bind to the antibodies on the test line forming analyte-antibody complex, which is further bound to conjugate particle-coupled antibody on the test line, forming a visible test line in the result window. In this case, a positive result is indicated by the presence of a test line. Presence of excess conjugate particles is desired, so that during detection, some of the conjugate particles are captured at the test line and continue to flow towards the second line of immobilized antibodies to a control line. This control line typically comprises a species-specific anti-immunoglobulin antibody, specific for the conjugate particle-coupled antibody. The control line gives information on integrity of the conjugate particle-coupled antibody and fluidics of the lateral flow unit.

To more clearly and concisely describe the subject matter of the disclosed application, the following definitions are provided for specific terms, which are used in the following description and the appended embodiments. Throughout the specification, exemplification of specific terms should be considered as non-limiting examples.

The singular forms "a", "an" and "the" include plural referents unless the context clearly dictates otherwise.

Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

As used herein, the term "lateral flow" means that a sample suspected of containing a target nucleic acid is placed on a test strip comprising a chromatographic material and the sample is wicked laterally through of the test strip by capillary action and binds to various reagents in the strip.

Accordingly, one embodiment of this invention provides a lateral flow assay device for detecting the presence or absence of a single-stranded target nucleic acid in a fluid sample, said device comprising a test strip having a first and second end and comprising: a sample receiving zone at or near said first end for receiving an aliquot of said sample and comprising a porous material having first and second oligonucleotide probes coupled to first and second binding partners, respectively, wherein said probes specifically hybridize to said target nucleic acid to form a complex having said first and second binding partners, said sample receiving zone being in lateral flow contact with a labeling zone comprising a porous material having at least a first visible moiety reversibly bound thereto and coupled to a first ligand which specifically binds to said first binding partner to form a visible complex, said labeling zone being in lateral flow contact with a capture zone comprising a microporous membrane which contains in a portion thereof a first capture moiety immobilized thereto which specifically binds said second binding partner, said capture zone being in lateral flow contact with an absorbent zone positioned at or near the second end of said test strip, wherein said visible complex is captured by said capture moiety in said portion of the capture zone. As used herein, the term "target nucleic acid" refers to the nucleic acid molecule that may be amplified or non-amplified for detection with the presented methods. The "target" molecule can be purified, partially purified, or present in an unpurified state in the sample.

As used herein, the term "test strip" refers to a chromatographic-like medium upon which an assay of this invention is preformed. Briefly, the test strip contains in sequential order a "sample receiving zone" at the proximal end for the application of the test sample, a "labeling zone" comprising visible moieties which are visible to the naked eye, a "capture zone" which contains an immobilized capture moiety that captures and retains the target nucleic acid, and an absorbent pad at the distal end to helps draw the sample through the test strip. The visible moieties provide means for detecting the presence of the target nucleic acid in the capture zone. The visible moieties are coupled to a ligand that specifically binds a binding partner coupled to or complexed with the target nucleic acid. These visible moieties bind the target nucleic acid as the fluid sample passes through the labeling zone and are carried to the capture zone by the liquid flow. When the target nucleic acid/visible moiety complex reaches the capture zone, a capture moiety, which is specific for a second binding partner coupled to or complexed with the target nucleic acid, captures and retains the complex.

As used herein, the term "oligonucleotide probe" refers to a nucleic acid which has a sequence complementary to a portion of the vaccine target nucleic acid and which is further coupled to a binding partner. The oligonucleotide probe may either be reversibly bound to the sample receiving zone of a test strip, and/or may be used to label the target nucleic acid prior to introduction to the lateral flow system as described herein (in the latter case the oligonucleotide probe is also referred to as a "primer").

The terms—"complementary" or "complementarity" are used in reference to nucleic acids (i.e., a sequence of nucleotides) related by the well-known base-pairing rules that A pairs with T and C pairs with G. For example, the sequence 5'-A-G-T-3', is complementary to the sequence 3'-T-C-A-5'. Complementarity can be "partial," in which only some of the nucleic acid bases are matched according to the base pairing rules. On the other hand, there may be "complete" or "total" complementarity between the nucleic acid strands when all of the bases are matched according to base pairing rules. The degree of complementarity between nucleic acid strands has significant effects on the efficiency and strength of hybridization between nucleic acid strands as known well in the art. This is of particular importance in detection methods that depend upon binding between nucleic acids, such as those of the invention. The term "substantially complementary" refers to any probe that can hybridize to either or both strands of the target nucleic acid sequence under conditions of high stringency as described below or, preferably, in polymerase reaction buffer, heated to about 95° C. and then cooled to about room temperature (e.g., 25° C.±3° C.). The probes may be reversibly bound to the sample receiving zone material directly by vacuum transfer, or by other well-known methods such as drying and desiccation. This embodiment, the oligonucleotide probe functions to label the target nucleic acid with a binding partner by hybridizing with it as it passes through the sample receiving zone of the test strip.

As used herein, the term "binding partner" refers to a member of a pair of molecules and/or compositions capable of recognizing a specific structural aspect of another molecule or composition, wherein the binding partners interact with each other by means of a specific, noncovalent or covalent interaction. Examples of such binding partners and corresponding molecules or compositions include, but are not limited to, any of the class of immune-type binding pairs, such as antigen/antibody or hapten/anti-hapten systems; and also any of the class of nonimmune-type binding pairs, such as biotin/avidin, biotin/streptavidin, digoxigenin/anti-digoxigenin F(ab'), folic acid/folate binding protein, complementary nucleic acid segments, protein A or G/immunoglo$\mu$lins, lectin/carbohydrate, substrate/enzyme, inhibitor/enzyme, virus/cellular receptor; and binding pairs which form covalent bonds, such as sulfhydryl reactive groups including maleimides and haloacetyl derivatives, and amine reactive groups such as isotriocyanates, succinimidyl esters and sulfonyl halides. Other binding partners include steroids, halogens and 2,4-dinitrophenyl. The labeling zone comprises a material that is capable of conducting lateral flow and is in lateral flow contact with the sample receiving zone. In certain embodiments, the labeling zone material is affixed to the capture zone membrane on the same side as the sample receiving zone. Materials suitable for the labeling zone material include, but are not limited to, porous or macroporous materials such as glass (e.g., borosilicate glass fiber), cotton, cellulose, polyester, polyethylene, rayon or nylon. The labeling zone comprises at least a first ("test") visible moiety (e.g., a colored microparticle or quantum dot) which is reversibly bound to the matrix and is coupled to a first ligand. In the present invention, the ligands are specific for discrete binding partners coupled to or complexed with amplified or non-amplified target nucleic acids. The labeling zone material must sufficiently retain the visible moieties in an anhydrous form prior to use of the lateral flow device, but must also release the visible moieties upon contact with the fluid sample and allow lateral flow of the target nucleic acid both before and after it becomes bound to the visible moiety.

The labeling zone material may also comprise a second visible moiety (i.e., a "control" visible moiety) which is reversibly bound to the labeling zone material. The control moiety is carried through to the capture zone along with the liquid flow. The control visible moiety does not contain a ligand specific for the target nucleic acid binding partner. Rather, the control visible moiety is coupled to a control ligand which binds its specific binding partner that is immobilized in a separate "control" portion of the capture zone. The control visible moiety is useful for verifying that the flow of fluid sample is as expected and that the microparticles have been successfully released from the labeling zone. The control visible moieties may be the same or a different color than the test visible moieties. If different colors are used, ease of reading the results is enhanced.

The capture zone membrane comprises a microporous material which is capable of conducting lateral flow and is in lateral flow contact with the labeling zone material. Materials suitable for the capture zone membrane include, but are not limited to, microporous materials having a pore size from about 0.01 μm to 10 μm, such as nitrocellulose, polyethersulfone, polyvinylidine fluoride, nylon, charge-modified nylon, and polytetrafluoroethylene. The capture zone comprises a test capture region comprising a first ("test") capture moiety that specifically binds a second binding partner coupled to or complexed with the target nucleic acid. That is, the test capture moiety and the second binding partner a member of a binding pair that specifically recognize each other. The arrangement of the first capture moiety in the capture zone may be, for example, in the form of a dot, line, curve, band, cross, or combinations thereof.

The capture zone may also contain a second ("control") capture moiety is a region which specifically binds the ligand coupled to the control visible moiety. The arrangement of the second capture moiety in region may be in the form of a dot, line, curve, band, cross, or combinations thereof, in one embodiment the immobilized second capture moieties are in a region that is separate from the region 108 that contains immobilized first capture moieties. Alternatively, the first and second capture moieties are contained within the same region. In this embodiment, the first and second visible moieties contain microparticles or quantum dots of different colors (e.g., blue and yellow), and the detection of a third color (e.g., green) in the capture zone indicates a positive result (i.e., the presence of the target nucleic acid). The control region is helpful in that appearance of a color in the control region signals the time at which the test result can be read, even for a negative result. Thus, when the expected color appears in the control region, the presence or absence of a color in the test region can be noted. Methods of immobilizing the capture moieties to the membrane are well known in the art. hi general, the test and control capture moieties can be dispensed onto the membrane as spaced parallel lines with a linear reagent dispensing system using a solution of the test capture moiety diluted with a suitable buffer and a solution of the control capture moiety diluted with a suitable buffer. The absorbent pad or zone is an absorbent material that is placed in lateral flow contact with the capture zone at the distal end of the test strip, the absorbent pad is affixed to the capture zone membrane on the same side of the membrane as the sample receiving zone and the labeling zone. The absorbent pad helps to draw a test sample from the sample receiving zone to the distal end of the test strip by capillary action. Examples of materials suitable for use as an absorbent pad include any absorbent material, include, but are not limited to, nitrocellulose, cellulose esters, glass (e.g., borosilicate glass fiber), polyethersulfone, and cotton.

In the embodiment the capture zone membrane is affixed to a rigid or semi-rigid support, which provides structural support to the test strip. The support can be made of any suitable rigid or semi-rigid material, such as poly(vinyl chloride), polypropylene, polyester, and polystyrene. The membrane may be affixed to the support by any suitable adhesive means such as with a double-sided adhesive tape. Alternatively, the support may be a pressure sensitive adhesive laminate, e.g., a polyester support having an acrylic pressure sensitive adhesive on one side that is optionally covered with a release liner prior to application to the membrane.

Support may optionally be affixed to a heating sheet. The heating sheet may be any material suitable for conducting heat to the test strip, such as copper, aluminum, or titanium. The heating sheet allows the lateral flow assays to be conducted at temperatures above room temperature, for example to increase the stringency of the assay or to determine Watson-Crick complementarity.

An alternative embodiment of a lateral flow device of this invention includes a sample receiving zone material, the labeling zone material, the capture zone membrane, and the absorbent pad are each affixed to a rigid or semi-rigid support. The sample receiving zone material overlaps with labeling zone material to allow for lateral flow contact therebetween. Similarly, the labeling zone material overlaps with the capture zone membrane, and the capture zone membrane overlaps with the absorbent pad. While it is not required that materials overlap, these materials must at least be in physical contact in the sequence such that the test sample can wick along the test strip without interruption. The support may optionally be affixed to a heating sheet. In another embodiment of this invention, test strip of the lateral flow devices of this invention are sheathed in a transparent film, provided that a portion of the sample receiving zone is left uncovered to allow application of the fluid sample to the test strip. For example, the test strip may be wrapped or sheathed using a clear polyester film having a pressure-sensitive adhesive coated on one side of the film by pressing the adhesive side of the film to all surfaces of the device except for a predetermined portion of the sample receiving zone. Other materials that could be used to wrap the device include any clear polymer that can withstand elevated temperatures (e.g., 95° C. or greater for at least 3-5 minutes) such as the temperatures used when the assay is performed in conjunction with the heating sheet. Thus, other examples of suitable wrapping materials include polycarbonates (e.g., Lexan), heat resistant acrylics (e.g., polymethylmethacrylate), butyrates (e.g., cellulose acetate butyrate), polystyrene, polypropylene, and glycol modified polyethylene terphthalate. If the lateral flow device comprises a support, the portion of the device wrapped in the film includes both the test strip and the support. Wrapping the device with a clear film helps to prevent contamination of the sample during an assay while still allowing visual monitoring of the capture zone.

This invention also provides a method for detecting the presence or absence of one or more target nucleic acids in a vaccine fluid sample. In certain embodiments, the method includes an unlabeled target nucleic acid is detected using a lateral flow device comprising two oligonucleotide probes reversibly bound to a membrane. The assay device comprises test strip having sample receiving zone. In this embodiment, sample receiving zone comprises a first oligonucleotide probe coupled to a first binding partner (A) and a second oligonucleotide probe coupled to a second binding partner (B). Prior to applying the fluid sample, which may contain the target nucleic acid, to the sample receiving zone, any nucleic acid present in the sample in a double stranded form is rendered single stranded by any denaturing method known in the art. The fluid sample is subsequently to the sample receiving zone. Alternatively, the target nucleic acid can be amplified prior to application to the sample receiving zone using any nucleic acid amplification method, such as those described herein. Test strip also contains a first visible moiety reversibly bound to the labeling zone material and coupled to ligand (A). Ligand (A1) is designed to specifically recognize and bind to binding partner (A) coupled to the first oligonucleotide probe. Test strip further comprises capture zone containing capture moieties (B') immobilized on the capture zone membrane. Capture moiety (B') is designed to specifically recognize and bind to binding partner B coupled to the second oligonucleotide probe.

The lateral flow diagnostic assays of the invention provide accurate and reliable results much faster than conventional methods. An assay of this invention typically provides a detectable results within 10 to 300 seconds from commencement. Further, the LFIA's and devices of this invention are able to provide direct detection of target nucleic acids without the need for amplification of the target nucleic acid prior to detection, provided that the sample contains the target nucleic acid in an amount that will provide a signal in the capture zone that can be detected with the naked eye. The assays of this invention can be performed under high or low stringency conditions. The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together. Those skilled in the art know that numerous equivalent conditions can be employed to comprise low stringency conditions. Hybridization under stringent conditions requires a perfect or near perfect sequence match. Hybridization under relaxed conditions allows hybridization between sequences with less than 100% identity. Greater stringency can be achieved by reducing the salt concentration or increasing the temperature of the hybridization.

As used herein, the term "rapid diagnostic test" (RDT) refers to testing of a biological sample, which can be carried out at the point of care to obtain a fast diagnosis. A RDT is a medical diagnostic test that is quick and easy to perform and can be carried out even in the absence of laboratory techniques such as microscopy, enzyme-linked immunosorbent assay (ELISA) or polymerase chain reaction (PCR). RDTs provide results within two hours, typically in approximately 15-30 minutes. By way of a non-limiting example, RDTs for vaccine authenticity typically require about 15-30 minutes from the time of vaccine sample collection to the time of obtaining a result. It will be understood that the time required for an RDT depends on variables such as the type of sample, the amount of sample, the nature of the analyte and the like.

Embodiments of a rapid diagnostic testing (RDT) device for testing of a vaccine sample is provided herein. The RDT device is compatible with equipment-free, point of care (POC) analyte-separation and detection process. For example, the RDT device provides rapid diagnostic testing by immunochromatographic separation and detection.

According to embodiments of the present invention, the RDT device comprises a channeled construct, at least one lateral flow unit, and a cassette housing. The channeled construct is configured to receive at least a portion of a vaccine sample for rapid separation of undesired materials from the sample and forms at least partially purified vaccine sample. The lateral flow unit comprises a sample receiving zone, a conjugate zone, and a detection zone. The sample receiving zone is operatively coupled to the channeled construct for receiving the partially purified vaccine sample from the channeled construct. The partially purified vaccine sample comprises at least one analyte. The conjugate zone is disposed adjacent to the first side of the sample receiving zone, wherein the conjugate zone comprises a conjugate particle for binding with the at least one analyte. The detection zone is disposed adjacent to the second side of the sample receiving zone. The detection zone comprises at least one binding agent for detecting the at least one analyte by capturing the analyte. Further, the lateral flow unit is at least partially disposed in the cassette housing. In some embodiments, the RDT device is employed for testing of a vaccine sample to determine the authenticity of the vaccine.

The lateral flow unit as employed for the present diagnostic testing device is a unit where liquid flows across the length of the lateral flow unit or lateral flow strip. The terms "lateral flow unit," or "lateral flow assay strip" may be used interchangeably throughout the specification. Traditionally designed lateral flow units are composed of a variety of materials, each serving one or more purposes, overlapping onto one another, mounted on a backing substrate (e.g. backing card) using a pressure-sensitive adhesive.

In certain embodiments, the sample receiving zone of the lateral flow unit is operatively coupled to the channeled construct for receiving one or more components of the vaccine sample. The one or more components received by the channeled construct may include an analyte of interest, which may be subsequently detected by the lateral flow unit. In embodiments the vaccine sample receiving zone is configured to receive vaccine sample from the channeled construct, where the vaccine sample comprises at least one analyte.

The conjugate particle may include colloidal gold, a colored particle, a fluorescent probe, a paramagnetic particle (such as paramagnetic monodisperse latex particle), a quantum dot, or a combination thereof. The RDT device may further include alternative conjugate reporters such as quantum dots included in cellulose nanobeads (CNB), magnetic beads, fluorescence tags, chemiluminescence molecules, or various shapes of quantum dot nanoparticles including nanospheres, nanorods, nanoshells. All such alternative conjugate reporters are contemplated within the scope of embodiments included herein. The conjugate particle is conjugated to one of the components of the vaccine sample, a component of the lateral flow assay strip (such as binding agent), or a biomolecule such as a protein. The protein may be an antigen or an antibody, depending on a format of the assay.

The detection zone is disposed adjacent to the second side of the sample receiving zone. The detection zone comprises at least one binding agent for detecting the at least one analyte by capturing the analyte. The detection zone may be constructed on a nitrocellulose membrane. In one embodiment, the detection zone may be formed by depositing one or more binding agents on the nitrocellulose membrane.

In certain embodiments, the analyte present in the vaccine is detected in the detection zone of the lateral flow strip. In some embodiments, the detection zone comprises a test region. The test region is a sub-zone of the detection zone where binding agents are deposited. In some embodiments, the test region is a test line on the lateral flow strip. The binding agents are typically proteins, such as antibodies or antigens, which serve to capture the analyte or the analyte-conjugate complex as they migrate to the test region, depending on the assay requirement. The detection zone further comprises a control region. In some embodiments, the test region is a control line on the lateral flow strip. One or more binding agents having affinity towards the conjugate particles but no have affinity towards the analyte are deposited on the control region. In some embodiments, the binding agent is one or more of an antibody, or a labeled antibody. As used herein, "labeled antibody" includes any antibody coupled to an enzyme or a substrate, which is capable of changing color on exposure to a substrate, or reagent (such as an enzyme), respectively. As such, the antibody may be labeled with a quantum dot, a dye, a metal particle (e.g., gold), a compound capable of producing chemiluminescence or fluorescence. In alternative embodiments, the antibody may be attached to a magnetic bead, a cellulose bead, a polymeric bead labeled with a quantum dot, dye, an affinity probe, and the like. In some embodiments, the binding agents are referred to as primary antibodies. In some alternative embodiments, the binding agents function as secondary antibodies.

In other embodiments, the contents of a vaccine are validated using an RDT device including sequence-dependent identification of the nucleic acid payloads via hybridization and lateral flow technology. In certain embodiments, an oligo near each end of the nucleic acid payload hybridized. In certain embodiments, hybridizations occur if a perfect match to sequence. In certain embodiments, one oligomer acts as the capture probe on the lateral flow test strip, and the other oligomer is labeled with quantum dots and acts as the detection probe.

In certain embodiments, the signal at the test line on the lateral flow strip occurs with nucleic acid of the correct sequence that is intact (i.e., not degraded or cleaved between the two probes).

In other embodiments, the invention encompasses antibody-based identification of vaccine delivery vehicle with lateral flow using traditional lateral flow technology with antibodies specific to lipids in the nanoparticle delivery (mRNA vaccines) or capsid proteins on the specific adenovirus delivery vehicle (AAV vaccines).

In various embodiments, the lateral flow devices of the invention include a variety of proteins that may be selectively chosen and fixed on a membrane and when an analyte-containing sample flows over a specific protein for which the analyte has affinity, binding is effected. Additionally, a label (e.g., a quantum dot) is used, typically adhered to the analyte, to effect signal generation for interpretation of positive results.

In certain embodiments, the sample receiving zone and the conjugate zone of the lateral flow unit are present on a common substrate. In such embodiments, the conjugate particle in the conjugate zone may be present at one end of the common substrate and the sample receiving zone may be present at the opposite end of the common substrate. In one embodiment, the common substrate further comprises a detection zone. In certain other embodiments, at least one of the vaccine sample receiving zone, the conjugate zone, and the detection zone of the lateral flow unit is constructed on a substrate that is different than a substrate on which the other zones are constructed. In one or more embodiments, the common substrate is selected from a glass fiber, a nitrocellulose, or a quartz. In one embodiment, the common substrate is a nitrocellulose membrane.

The lateral flow unit further comprises a buffer reservoir disposed adjacent to the conjugate zone. The buffer reservoir is disposed such that when the RDT device is in operation, the buffer added to the buffer reservoir passes through the conjugate zone of the lateral flow unit. In some embodiments, the buffer reservoir is disposed on one end of the lateral flow unit. In one or more embodiments, a buffer solution may be added to the buffer reservoir. In some alternative embodiments, buffer reagents may be impregnated in the buffer reservoir, where the impregnated buffer reagents may be reconstituted as a buffer solution by adding water. The vaccine sample comprising at least one analyte received by the sample receiving zone is chased with the buffer from the buffer reservoir to the different zones of the lateral flow unit. In operation, at least a portion of the buffer is passed from the conjugate zone to the sample receiving zone, and subsequently to the detection zone of the lateral flow unit. In one or more embodiments, the buffer reservoir comprises a non-lytic buffer. In some other embodiments, the buffer reservoir comprises a buffer with a surfactant concentration of less than about 0.01 mM.

In one or more embodiments, the lateral flow unit further comprises a wicking pad or an absorbent pad. The wicking pad is disposed adjacent to the detection zone. In some embodiments, the wicking pad is disposed adjacent to the detection zone and at the one end of the lateral flow unit. The wicking force of the wicking pad acts as a driving force to facilitate the buffer to flow through the lateral flow unit along a direction represented by reference numeral. The wicking pad draws the buffer to flow towards the wicking pad based on the strong wicking force. When excess conjugate particles move past the test region of the detection zone, the excess conjugate particles are entrapped in the wicking pad.

The RDT device may be operated in different ways, depending on the assay design, selection of conjugate particles, or selection of antibodies. In some embodiments, the conjugate zone comprises conjugate particles which are coupled to a primary antibody. In some of these embodiments, when buffer laterally flows from the buffer reservoir to the conjugate zone, the buffer remobilizes the dried primary antibody coupled-conjugate particles and subsequently flows to the sample receiving zone. Once the primary antibody-coupled conjugate particle and an analyte are in contact in the sample receiving zone, the primary antibody-coupled conjugate particle binds to the analyte to form a primary antibody-coupled conjugate-analyte complex.

The primary antibody-coupled conjugate-analyte complex along with remaining free conjugate particles and analyte particles may then migrate to the detection zone of the lateral flow unit. The detection zone is configured for detecting the analyte by capturing the primary antibody-coupled conjugate-analyte complex. In the detection zone, the binding agents, such as secondary antibodies disposed in the test region interacts with the conjugate-analyte complex. The secondary antibody binds to the primary antibody, where the primary antibody is coupled to the conjugate particle of conjugate-analyte complex. On binding of the secondary antibody to the primary antibody-coupled conjugate-analyte complex, a signal is generated at the test region, which is typically measured for detection of analyte.

In some alternative embodiments, the conjugate zone comprises conjugate particles which are coupled to secondary antibodies. In some of these embodiments, the test region of the detection zone comprises the binding agents that are primary antibodies specific to the analyte of interest. When buffer flows from the first end to the second end of the lateral flow unit, first, the analyte reaches the test region of the detection zone and is captured by the primary antibody disposed in the test region and forms primary antibody-analyte complex. Secondly, the secondary antibody coupled-conjugate particles traverse along with the buffer and reach the test region of the detection zone. The steps of capturing analyte by the primary antibody and traversing the secondary antibody coupled-conjugate particles along with the buffer from conjugate zone to the detection zone may occur simultaneously or consecutively. In the test region, once the secondary antibody coupled-conjugate particle is in contact with the primary antibody-analyte complex, the secondary antibody coupled-conjugate particle binds to the primary antibody-analyte complex. On binding of the secondary antibody coupled-conjugate particle to the primary antibody-analyte complex, a signal is generated at the test region, wherein presence of the signal is typically measured for detection of analyte.

The present RDT device of the subject specification advantageously allows for testing of larger volumes of samples compared to the sample used for currently available RDT devices. In some embodiments, a volume of vaccine sample employed for the present RDT device may be in a range from about 50 µL to about 200 µL. In some embodiments, a volume of the vaccine sample used for rapid diagnostic testing is in a range from about 75 µL to about 150 µL. In some other embodiments, a volume of the vaccine sample used for rapid diagnostic testing is in a range from about 90 µL to about 120 µL. The ability of an RDT device to process larger sample volume indicates that a larger volume of analyte reaches the lateral flow unit while using the present RDT device, which results in improving the signal intensity of the RDT device. In contrast, the sample read-out is affected by using the currently available RDT devices which are typically suitable for analyzing less amount of sample, such as about 5 µL of vaccine sample. The 100 µL vaccine sample comprising at least one analyte is subsequently transferred to the lateral flow unit for analyte detection.

The RDT assay results using the RDT device are interpreted based on the presence or absence of a signal at the test region on the lateral flow unit. The RDT assay is determined visually or by using a reader to measure the signal intensity generated at the test region. The reader may include a plate reader, a spectrophotometer, a fluorescence spectrophotometer, reader for measuring chemiluminescence, and the like. The higher signal intensity is advantageous for detection of analytes because generally RDTs rely on visually detected changes in color of the test region on a lateral flow unit. A faint color change is not visually detectable and could lead to a false negative result on the RDT device.

In some embodiments, the channeled construct comprises a size exclusion separation element. In one embodiment, the first surface of the size exclusion separation element is substantially planar with a raised edge surrounding the first surface of the size exclusion separation element. At least a portion of the second surface of the size exclusion separation element is in direct contact with a first surface of the lateral flow unit that comprises the sample receiving zone, conjugate zone, and detection zone.

In some embodiments, the size exclusion separation element may include a membrane, a chromatographic column, chromatographic beads, or a combination thereof, for rapid separation and delivery of a biological sample. In some other embodiments, the size exclusion separation element comprises progressively narrowing channels (elongated pores). In some embodiments, the size exclusion separation element is a porous membrane.

The size exclusion separation element, such as a porous membrane of the channeled construct ensures rapid separation of undesired materials from the vaccine sample to form at least partially purified biological sample comprising at least one analyte. Followed by purification, the channeled construct also delivers the partially purified biological sample to the lateral flow unit. In some embodiments, the porous membrane employed for the channeled construct is selected from an asymmetric porous membrane, a membrane comprising affinity surfaces, a membrane comprising hydrophobic cores, or a membrane comprising charged surfaces.

In some embodiments, the channeled construct comprises an asymmetric porous membrane having pores with asymmetric distribution. The asymmetric porous membrane has a first surface and a second surface. The asymmetric porous membrane 40 has an upstream side and downstream side. The asymmetric porous membrane is disposed on the channeled construct such that the upstream side and downstream side of the asymmetric porous membrane are aligned with the upstream side and downstream side of the channeled construct, respectively.

The pores having larger average pore-diameter as shown in first surface are on the upstream side of the asymmetric porous membrane act as a pre-filter for the separation of large particles, such as larger particles of vaccine sample. The pores having smaller average pore-diameter as shown in second surface present on the downstream side of the asymmetric porous membrane act as an exclusion zone or cut-off layer to further filter smaller particles from the fluid. For example, the said distribution of pores allows a size-based filtration whereby larger particles are retained in/on the membrane, while the smaller analytes flow through the membrane. Asymmetric porous membranes may comprise a single layer or multiple layers. The pore size ratio of asymmetric porous membranes may vary depending on the sample being filtered.

In some embodiments, the asymmetric porous membrane is manufactured using a laser cutting technique that leaves a ridge along the cut edge. In some embodiments, the asymmetric porous membrane is cut during manufacture by die cut techniques. In some embodiments, an asymmetric porous membrane is cut using knife cut techniques.

In some embodiments, the asymmetric porous membrane is a polyethersulfone membrane, a polysulfone membrane, a glass fiber, a nylon membrane, a polyester membrane, a polycarbonate membrane, a polypropylene membrane, a polyvinylidene difluoride membrane, a cellulose membrane, a nitrocellulose membrane, a cellulose acetate membrane, a nitrocellulose mixed ester membrane, a polyurethane membrane, a polyphenylene oxide membrane, a poly(tetrafluoroethylene-co-hexafluoropropylene membrane, a cellulose phosphate membrane, a cellulose/silica gel paper, a borosilicate glass membrane, a quartz membrane, or a combination thereof. In a specific embodiment, the asymmetric porous membrane is an asymmetric polysulfone membrane. In another specific embodiment, the asymmetric porous membrane is an asymmetric polyethersulfone membrane.

In some embodiments, the size exclusion separation element of the channeled construct is designed as a plurality of conical shaped channels. Each of the channel has a smaller average pore diameter at the bottom of the channel than the average pore diameter at the top of the channel. In some embodiments, each of the channels has an average pore diameter of about 10 microns to about 100 microns on the first surface 36 and an average pore diameter of about 1 micron to about 3 microns on the second surface of the asymmetric porous membrane. In certain embodiments, the channeled construct is made of a polymer, a ceramic, a glass, a metal, or a combination thereof.

In some alternative embodiments, the size exclusion separation element is disposed at a determined angle with respect to the lateral flow unit. In this example, the size exclusion separation element is disposed parallel to the lateral flow unit. In some of such embodiments, the parallelly disposed size exclusion separation element comprises a cellulose membrane, a nitrocellulose membrane, a glass fiber membrane, a quartz membrane, a borosilicate glass membrane, a mixed cellulose ester membrane, a polyvinylidene difluoride membrane, or a combination thereof, disposed laterally relative to the lateral flow unit.

In some embodiments, the flow of the biological sample from the channeled construct to the lateral flow unit may be pressure-driven. The pressure may be generated after closure of the housing of the device, by capillary force, by gravity, in an electric field, or by any combination thereof. Similarly, the flow may be initiated by any such method that initiates contact of the biological sample with the sample pad, test region and/or control line of the lateral flow unit including manually applied pressure.

The lateral flow unit is at least partially disposed in a cassette housing, wherein the cassette housing ensures an efficient fluidic transfer from channeled construct to the lateral flow unit with a minimal loss of the biological sample. The use of the cassette housing is advantageous especially when a large volume of a vaccine sample is applied to the RDT device. The lateral flow unit and the channeled construct are disposed in the cassette housing and arranged such that the chances of sample loss are reduced significantly.

In one or more embodiments, the sample well of the cassette housing comprises at least one wall forming a channel with a top aperture and a bottom aperture, where the bottom aperture includes a flange. The bottom aperture of the cassette housing is positioned to form a gap between the bottom aperture and the channeled construct. The flange of the bottom aperture is positioned to contact the channeled construct.

The cassette housing having a first surface and a second surface, further comprises a plurality of rib structure. In some embodiments, the plurality of rib structure includes two different series of rib structure. A series of rib structure extending from the first surface of the cassette housing, referred to herein as a "first series of rib structures". The first series of rib structures are positioned adjacent to the sample well. The first series of rib structure is positioned such that a gap is formed between each of the rib structures and the sample well. The first series of rib structure is also in contact with the channeled construct.

In an alternative embodiment, the cassette housing is opened and a channeled construct is placed adjacent to the lateral flow unit such that one edge (proximal end) of the channeled construct contacts the lateral flow unit. The other edge of the channeled construct (distal end) placed adjacent to the sample well for receiving the biological sample.

In addition to authenticating a vaccine, the rapid diagnostic testing devices described herein are applicable to a variety of RDTs including RDTs for detection of viruses, infectious diseases, bacteria, cancers, cardiac problems, animal diseases, sexually transmitted diseases, forensics, and the like.

The rapid diagnostic testing devices described herein may also be further adapted by including additional components such as colorimetric readers, photothermal readers, fluorescence readers, chemiluminescence readers, magnetic readers and the like. While typical RDTs are immune-chromatographic assays which rely on antibody conjugates, dye labeled antibodies, or sandwich assays for detection, other methods of detection are contemplated within the scope of embodiments described herein including and not limited to colorimetric particles (metal particles, polymeric beads labeled with dyes, etc.), fluorescence, chemiluminescence, magnetic beads and the like. In addition to antibody capture, the analyte may be captured by techniques such as nucleotide/aptamer binding and such variants are contemplated as being within the scope of embodiments presented herein. It will be recognized that there are many types of assays such as competitive and non-competitive assays and such variations are also contemplated as being within the scope of embodiments presented herein. Further, multiple detection strips, and/or strips with multiple detection lines may be employed in the devices and methods described herein.

In certain embodiments, the invention encompasses a means to authenticate vaccine packaging including quantum-dot QR codes on the packaging of vaccines to verify source using an ultraviolet flashlight.

While only certain features of the invention have been illustrated and described herein, many modifications and changes will occur to those skilled in the art. It is, therefore, to be understood that the appended embodiments are intended to cover all such modifications and changes as fall within the scope of the invention.

The invention claimed is:

1. A rapid diagnostic testing device for rapid authentication of a COVID-19 vaccine, comprising: a sample receiving zone, wherein the sample receiving zone comprises a first side and a second side; a conjugate zone disposed adjacent to the first side of the sample receiving zone, wherein the conjugate zone comprises a conjugate particle comprising at least one of quantum dot or metal nanocluster biolabels for binding with the analyte; and a detection zone disposed adjacent to the second side of the sample receiving zone, lateral flow assay device configured for detecting the presence or absence of at least one single-stranded target nucleic acid in a fluid sample; wherein said probes are configured specifically hybridize to said target nucleic acid to form a complex having said first and second binding partners, said sample receiving zone being in lateral flow contact with a labeling zone comprising a porous material having at least a first visible moiety reversibly bound thereto and coupled to a first ligand which specifically binds to said first binding partner to form a visible complex, said labeling zone being in lateral flow contact with a capture zone comprising a microporous membrane which contains in a portion thereof a first capture moiety immobilized thereto which is configured to specifically binds said second binding partner, said capture zone being in lateral flow contact with an absorbent zone positioned at or near the second end of said device, wherein said visible complex is captured by said capture moiety in said portion of the capture zone, wherein the labeling zone includes one or more quantum dots; wherein said rapid diagnostic testing device is configured for rapid authentication of a COVID-19 vaccine.

2. A method for authenticating the veracity of a COVID-19 vaccine, which vaccine includes a nucleic acid comprising contacting a sample of vaccine with a lateral flow assay device, which lateral flow assay device is used for detecting the presence or absence of at least one single-stranded target nucleic acid in a fluid sample, said device having a first and second end and comprising:

a sample receiving zone at or near said first end for receiving an aliquot of said sample and comprising a porous material having first and second oligonucleotide probes coupled to first and second binding partners, respectively, wherein said probes specifically hybridize to said target nucleic acid to form a complex having said first and second binding partners, said sample receiving zone being in lateral flow contact with a labeling zone comprising a porous material having at least a first visible moiety reversibly bound thereto and coupled to a first ligand which specifically binds to said first binding partner to form a visible complex, said labeling zone being in lateral flow contact with a capture zone comprising a microporous membrane which contains in a portion thereof a first capture moiety immobilized thereto which specifically binds said second binding partner, said capture zone being in lateral flow contact with an absorbent zone positioned at or near the second end of said device, wherein said visible complex is captured by said capture moiety in said portion of the capture zone, wherein the labeling zone includes one or more quantum dots.

3. The method of claim 2, wherein said sample receiving zone porous material retains said probes prior to contact with said fluid sample and releases said probes after contact with said fluid sample.

4. The method of claim 3, wherein said sample receiving zone porous material is selected from the group consisting of glass, cotton, cellulose, polyester, rayon, nylon, polyethersulfone, and polyethylene.

5. The method of claim 2, wherein said first and second binding partners are selected from the group consisting of antibodies or fragments thereof, proteins, haptens, antigens or fragments thereof, avidin, streptavidin, biotin, fluorescein, isothiocyanate, folic acid, folate binding protein, protein A, protein G, immunoglobulins, digoxigenin, anti-digoxigenin F(ab')2, complementary nucleic acid segments, protein A, protein G, immunoglobulins, lectin, carbohydrate, enzymes, viruses, maleimides, haloacetyl derivatives, isotriocyanates, succinimidyl esters, sulfonyl halides, steroids, halogens and 2,4-dinitrophenyl.

6. The method of claim 2, wherein said labeling zone porous material is selected from the group consisting of glass, cotton, cellulose, polyester, polyethylene, rayon or nylon.

7. The method of claim 2, wherein said first visible moiety comprises a ligand coupled to one or more microparticle.

8. The method of claim 7, wherein said microparticle is selected from the group consisting of polymers or copolymers of olefinically unsaturated monomers, glass, acrylamide, methacrylate, nylon, acrylonitrile, polybutadiene, metals, metal oxides and their derivatives, dextran, cellulose, liposomes, red blood cells, pollens, quantum dots, and bacteria.

9. The method of claim 2, wherein said capture zone membrane comprises a microporous material selected from the group consisting of nitrocellulose, polyethersulfone, polyvinylidine fluoride, nylon, charge-modified nylon, and polytetrafluoroethylene.

10. The method of claim 2, wherein said first capture moiety is selected from the group consisting of antibodies or fragments thereof, proteins, haptens, antigens or fragments thereof, avidin, streptavidin, biotin, fluorescein isothiocyanate, folic acid, folate binding protein, protein A, protein G, immunoglobulins, digoxigenin, anti-digoxigenin F(ab')2, complementary nucleic acid segments, protein A, protein G, immunoglobulins, lectin, carbohydrate, enzymes, viruses, maleimides, haloacetyl derivatives, isotriocyanates, succinimidyl esters, sulfonyl halides, steroids, halogens and 2,4-dinitrophenyl.

11. The method of claim 2, wherein said capture zone is prepared by applying a solution containing said capture moiety to said membrane under conditions wherein the capture moiety becomes immobilized on said membrane, followed by drying said membrane.

12. The method of claim 11, wherein said solution is applied to said membrane in the form of a line.

13. The method of claim 2, wherein said labeling zone further comprises a second visible moiety reversibly affixed to said matrix and coupled to a second ligand, and said capture zone further comprises in a portion thereof a second capture moiety immobilized thereon which specifically binds said second ligand.

14. The method of claim 13, wherein said portion of said capture zone containing said first capture moiety is separate from said portion containing second capture moiety.

15. The method of claim 2, wherein said absorbent zone comprises a material selected from the group consisting of nitrocellulose, cellulose esters, glass, polyethersulfone, and cotton.

16. The method of claim 2, wherein said entire test strip except for a portion of said sample receiving zone is completely sheathed in a transparent film.

\* \* \* \* \*